(12) United States Patent
Acharya et al.

(10) Patent No.: US 6,307,910 B1
(45) Date of Patent: Oct. 23, 2001

(54) METHODS AND APPARATUS FOR REDUCED RADIATION CORONARY COMPUTED TOMOGRAPHY IMAGING

(75) Inventors: Kishore C. Acharya; Jiang Hsieh, both of Brookfield; Kenneth G. Dunahee, Muskego; Steven J. Woloschek, Franklin, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/479,015

(22) Filed: Jan. 7, 2000

(51) Int. Cl.$^7$ ........................................ H61B 6/03
(52) U.S. Cl. .................................. 378/4; 378/21
(58) Field of Search ................... 378/4, 21, 15, 378/19

(56) References Cited

U.S. PATENT DOCUMENTS 6,108,575 * 8/2000 Besson ........................... 600/425
6,173,032 * 1/2001 Besson ............................ 378/19
6,226,350 * 5/2001 Hsieh ............................. 378/98

* cited by examiner

Primary Examiner—Robert H. Kim
Assistant Examiner—Irakli Kiknadze
(74) Attorney, Agent, or Firm—Armstrong Teasdale, LLP; Christian G. Cabou

(57) ABSTRACT

Methods and corresponding apparatus for imaging a portion of a patient's body with a computed tomographic imaging system configured to scan the patient's body at a cyclically varying view angle, in which the imaging system includes a radiation source and detector array providing a fan angle width of image data. In one embodiment, the method includes axially scanning the portion of the patient's body, gating the radiation source on over less than a 360° view angle cycle of the axial scan, acquiring image data of the portion of the patient's body during at least a portion of the time the radiation source is gated on, and assembling the acquired image data into an image of the portion of the patient's body.

40 Claims, 5 Drawing Sheets

METHODS AND APPARATUS FOR REDUCED RADIATION CORONARY COMPUTED TOMOGRAPHY IMAGING

BACKGROUND OF THE INVENTION

This invention relates generally to methods and apparatus for computed tomography imaging, and more particularly to methods and apparatus for computed tomography imaging with physiological gating to reduce motion artifacts and patient radiation exposure.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In one known system, to reduce artifacts to an acceptable level, an entire scan is performed in a fraction of cardiac cycle with an electron beam CT (EBCT) imaging device. In an EBCT imaging device, x-ray emissions generated by a scanning electron beam are used for imaging. Physical rotation of a gantry is eliminated, and a scan of the electron beam can be completed in as little as 50 milliseconds to essentially completely freeze cardiac motion for coronary imaging. However, the known EBCT imaging device is considerably more expensive than conventional CT imaging devices and is not available in many hospitals. Moreover, the known EBCT imaging device images only a single slice of a volume at a time. Thus, repeated radiation doses are required to provide comprehensive three-dimensional coverage of a volume, squandering at least a substantial portion of any potential reduction of patient radiation dose.

It would therefore be desirable to provide methods and apparatus for computed tomography imaging that reduce motion artifacts utilizing less expensive radiation systems. It would also be desirable to provide such methods and apparatus that reduce patient radiation exposure during imaging.

BRIEF SUMMARY OF THE INVENTION

There is therefore provided, in one embodiment, a method for imaging a portion of a patient's body with a computed tomographic imaging system configured to scan the patient's body at a cyclically varying view angle, in which the imaging system includes a radiation source and detector array providing a fan angle width of image data. The method includes the steps of axially scanning the portion of the patient's body, gating the radiation source on over less than a 360° view angle cycle of the axial scan, acquiring image data of the portion of the patient's body during at least a portion of the time the radiation source is gated on, and assembling the acquired image data into an image of the portion of the patient's body.

Because the radiation source is gated on over less than a 360° view angle cycle, a reduction in patient radiation exposure is achieved. Moreover, when applied to a cyclically moving body part, such as a heart, this reduction in radiation exposure is accompanied by a reduction in motion-induced artifacts when image data is appropriately collected during times that the radiation source is gated on.

DETAILED DESCRIPTION OF THE INVENTION

Figure 1:
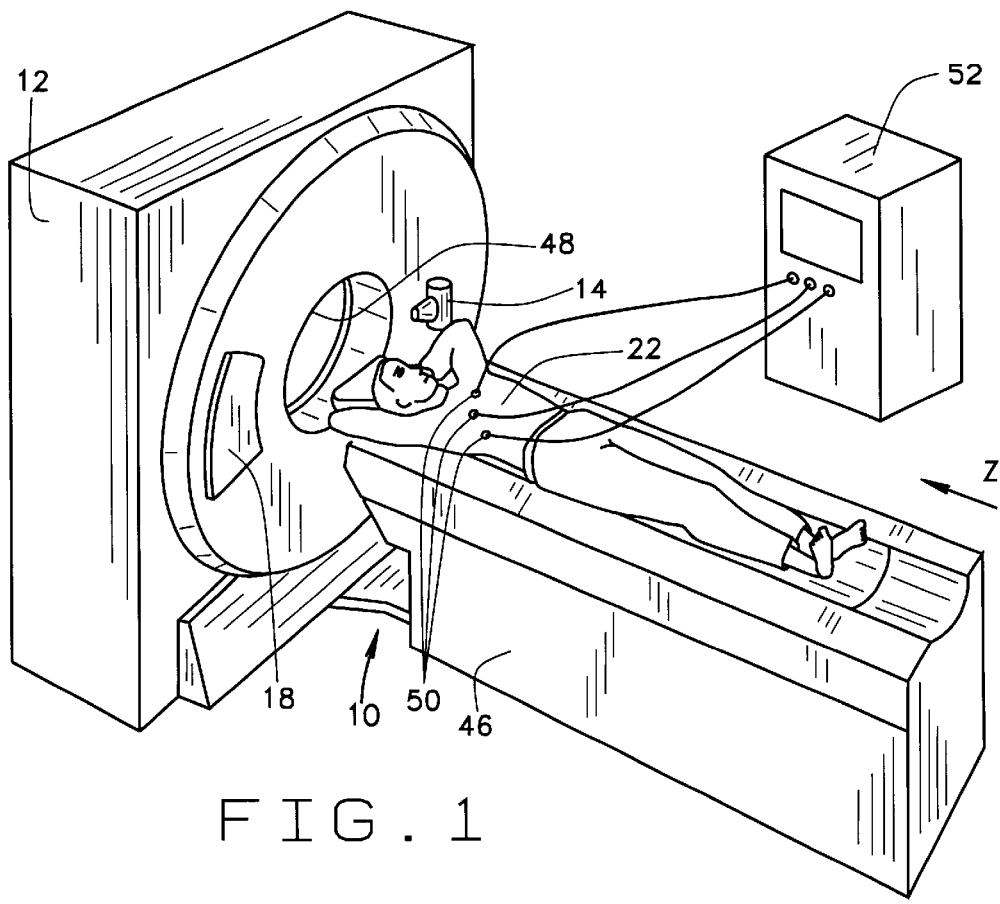
FIG. 1 is a pictorial view of a CT imaging system.
Figure 2:
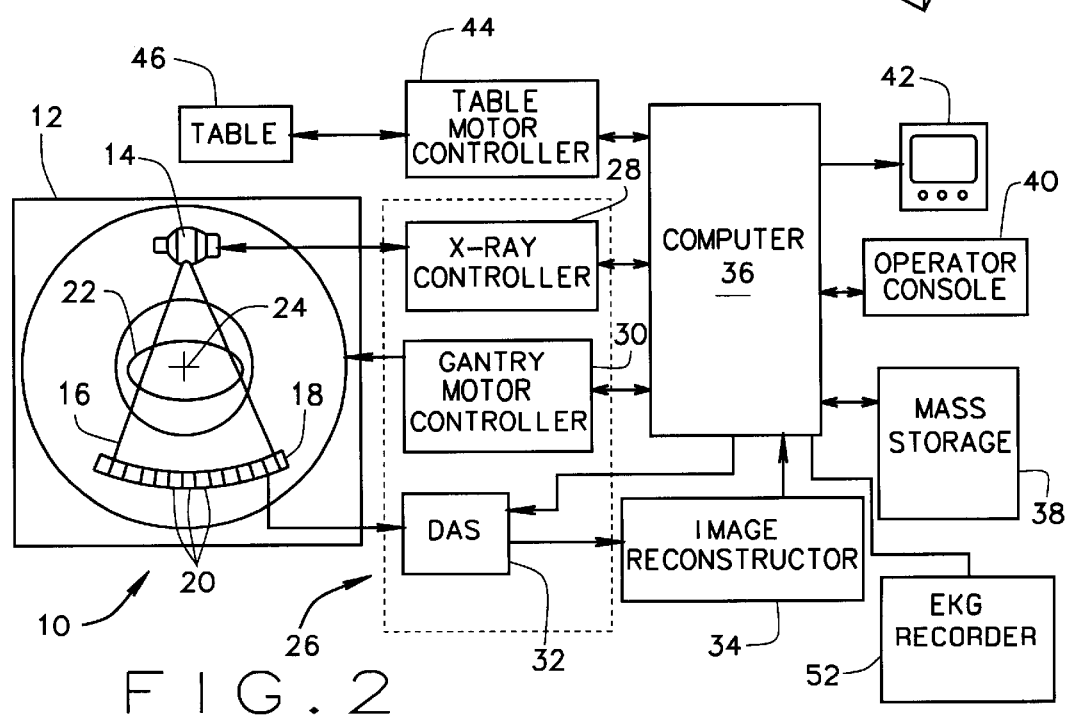
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a fan-shaped beam of x-rays 16 toward a detector array 18 on the opposite side of gantry 12. Detector array 18 is formed by detector elements 20 that are spread across a fan angle. Together, detector elements 20 sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48 in a z-axis direction. To measure a cardiac cycle of patient 22, EKG probes 50 are attached to patient 22. An EKG is measured by EKG machine 52.

In one embodiment of the present invention, a portion of a body of patient 22 is axially scanned, i.e., table 46 does not move patient 22 while radiation source 14 is on and image data is being acquired. To reduce radiation exposure during imaging, radiation source 14 is gated on by computer 36 only during a portion of a gantry angle rotation during an axial scan of a portion of the body of patient 22. Thus, radiation source 14 is gated on over less than a 360° view angle cycle of the axial scan. Image data is acquired only for a period during which radiation source 14 is gated on, for example, during all of, or only during a portion of a period during which radiation source 14 is on. In one embodiment, radiation source 14 is gated on for a period longer than image data is acquired, thus making it easier to accommodate variations in a heart rate of patient 22.

In one embodiment, a single-slice imaging system 10 is used to image a body portion of patient 22 having a cyclical motion, for example, the heart. An axial "half scan" is divided into N sectors, where N is a positive integer, for example, greater than or equal to 2. As used herein, a "half scan" is a view angle range equal to 180° plus a fan angle. Image data representing at least a half scan is acquired by acquiring image data corresponding to each of the N sectors during corresponding portions of a cardiac cycle of patient 22 over at least N cardiac cycles. In this embodiment, no more than one sector is acquired per cardiac cycle. (In another embodiment in which imaging system 10 is a multi-slice imaging system, no more than one sector of each slice is collected per cardiac cycle.) Each sector obtained during a cardiac cycle is acquired in a relatively short period of time during substantially the same portion of the cardiac cycle, so that combining these short, scanned sectors from these portions of different cardiac cycles results in reduced motion artifacts in the final image. By "substantially the same portion of the cardiac cycle," it is meant that a difference in the heart's position during these portions of the cardiac cycle are so similar that any differences in position of the heart do not, by themselves, result in degradation of an assembled image of consequence for diagnostic or medical purposes. Steps of gating radiation source 14 and acquiring a sector of image data are repeated at least until image data representative of a half scan of one image slice is acquired.

Figure 3:
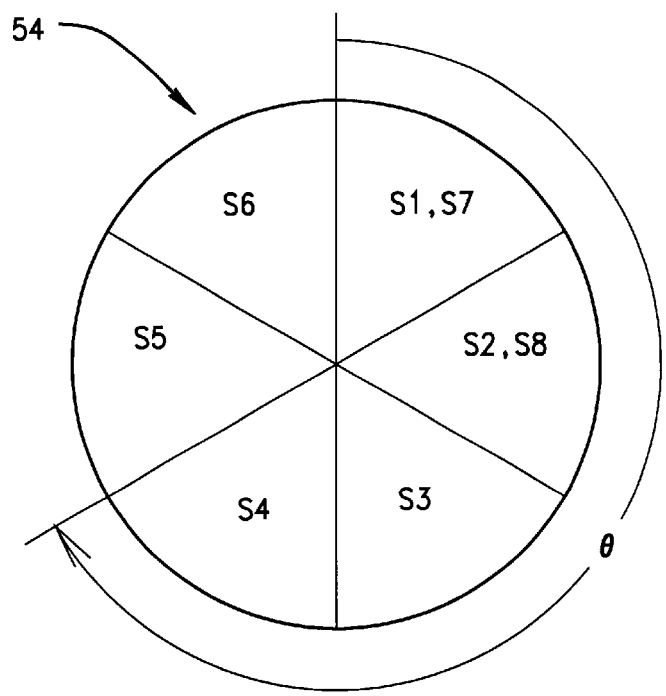
FIG. 3 is a schematic illustration of a 360° axial scan, a half scan, and a set of image acquisition sectors for fan para geometry reconstruction.

For example, referring to FIG. 3, an axial scan 54 is represented. In this example, in which a fan-para (parallel) sampling geometry is utilized, an axial half scan angle of 240°, i.e., 180° plus a fan angle of 60°, is represented as angle $\theta$. Half scan angle $\theta$ is divided into N=4 main view angle sectors S1, S2, S3, and S4. Also shown in FIG. 3 are respective "opposing" view angle sectors S5, S6, S7, and S8. Insofar as data collection is concerned, it makes little difference whether data representing a main view angle sector or its respective opposing view angle sector is acquired. Therefore, in one embodiment, the acquired sectors include at least one main view angle sector and at least one opposing sector, but only one of a main view angle sector and its corresponding opposing sector is acquired. For example, image data for opposing sector S5 is acquired and used in place of image data for main view angle sector S2.

In the embodiment illustrated in FIG. 3, because the axial half scan angle is greater than 180°, some of the opposing view angle sectors overlap some of the main view angle sectors. View angle sectors S7 and S8 exactly coincide with the main view angle sectors S1 and S2, respectively, because 240°/N happens to precisely divide 360°. Opposing view angle sectors do not coincide with main view angle sectors in every embodiment.

FIG. 3 shows a starting angle of 0° for the first sector. However, in any particular case, it will be recognized that the first sector can start at any angle based, for example, on scanning speed and cardiac rate. Any resulting offset would be added to each of the angles illustrated in FIG. 3.

Figure 4:
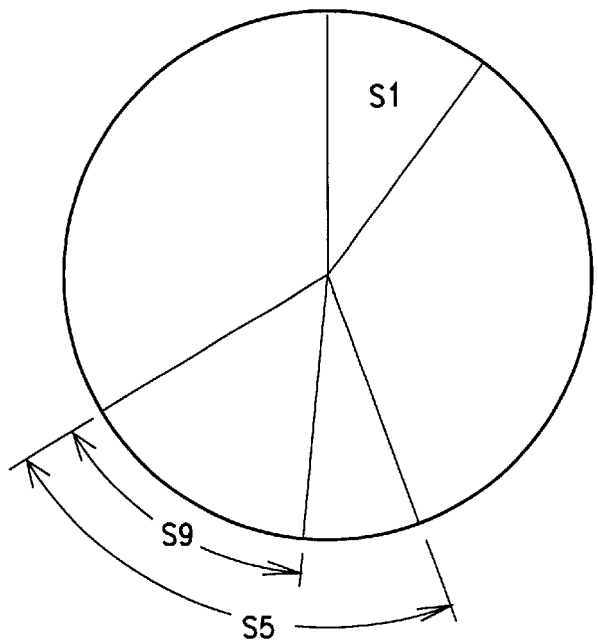
FIG. 4 is a schematic illustration of a 360° scan, showing a main view angle sector, a full-size opposing view angle sector, and a reduced-size opposing view angle sector.

For fan-beam geometry (as opposed to fan-para geometry), half scan angle $\theta$ divided is also divided by N, where N is a number of main view angle sectors. N is selected in advance according to spatial resolution criteria. Referring to FIG. 4, each full-size opposing sector S5 has a size equal to the size of its corresponding main view angle sector S1 plus a fan angle when fan-beam geometry is utilized. Therefore, acquisition times for any opposing sector is longer than that of a corresponding main view angle sector. However, because cardiac imaging requires only smaller imaging regions (e.g., 25 cm field of view out of a 50 cm full field of view), smaller opposing sector sizes can be used. In one embodiment, for example, reduced opposing sectors S9 as small as the corresponding main view angle sector S1 size plus one-half of the fan angle suffice.

Figure 5:
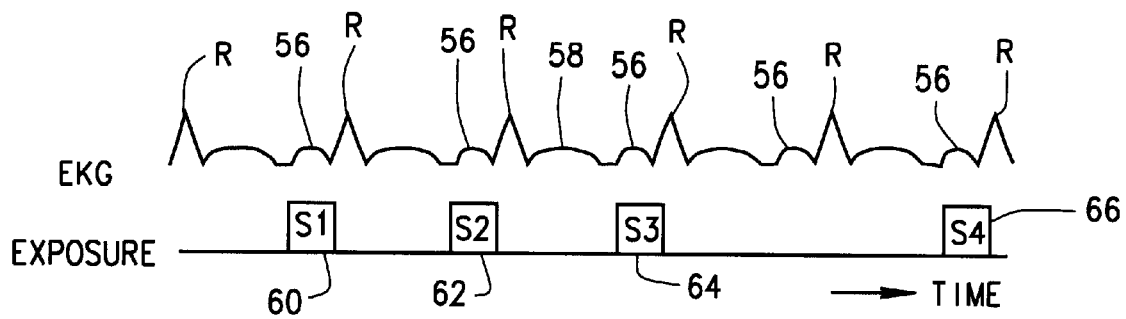
FIG. 5 is a drawing of an electrocardiogram (EKG) signal, showing times during which view angle sectors of data representative of images are acquired.

In one embodiment, cardiac imaging employs imaging system 10 in axial scanning mode, in which table 46 does not move while patient 22 is exposed to x-ray beam 16 for imaging. Because table 46 does not move in axial scanning, acquisition of image data can wait, if necessary, until gantry 12 is in position to obtain a needed sector of image data at a time when the heart of patient 22 is in a selected part of its cardiac cycle. For example, referring to FIG. 5, a selected portion 56 of a cardiac cycle, as indicated by EKG signal 58, occurs before an R-peak of the cardiac cycle. Image data for sector S1 is obtained at 60, for sector S2 at 62, and for sector S3 at 64. However, gantry 12 is not in a proper position to obtain the view angles required for sector S4 during the next portion 56 of the cardiac cycle. Thus, for example, computer 36 is configured to determine whether to collect each sector depending upon a range of view angles during which radiation source 14 is gated on and a cyclical motion of a body of patient 22 represented in this embodiment by EKG 58. One or more cardiac cycles are skipped until gantry 12 is in a proper position. Image data for sector S4 is obtained at when gantry 12 is next in a proper position, as at 66.

Scan protocols for acquiring data sectors are defined by three parameters: S, a number of slices acquired by data acquisition system 10; I, a stepping or indexing distance that table 46 is advanced between sector acquisitions, expressed as a multiple of a slice thickness; and N, a number of sectors selected for dividing a half-angle scan. All three parameters are integers that satisfy the following inequalities: $S \geq 1$; $S \geq I \geq 0$; and $N \geq 1$. For an embodiment in which I=0, a table 46 position is held constant until all N sectors have been acquired. If additional slices of image data are to be acquired, table 46 position is incremented (i.e., stepped or indexed) by S slices in a prescribed direction. Effectively, the body of patient 22 is stepped or indexed by incrementing table 46, so that another slice of image data is obtained. In this embodiment, there is no restriction on an order in which the N sectors of a slice are collected. For example, slices can be collected in an order S1, S3, S2, S4.

Figure 6:
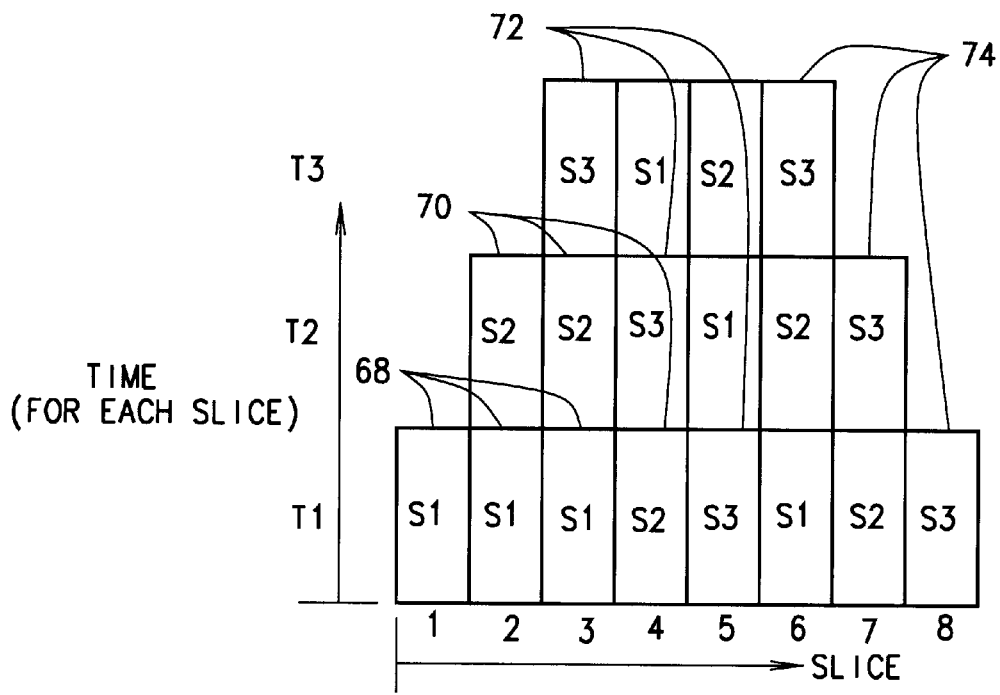
FIG. 6 is a drawing representing view angle sector acquisition in an embodiment in which S, a number of slices being acquired at one time, is equal to 3; I, a stepping or indexing distance expressed as a multiple of a slice thickness, is equal to 1; and N, a number of view angle sectors selected for dividing a half angle scan, is equal to 3.
Figure 7:
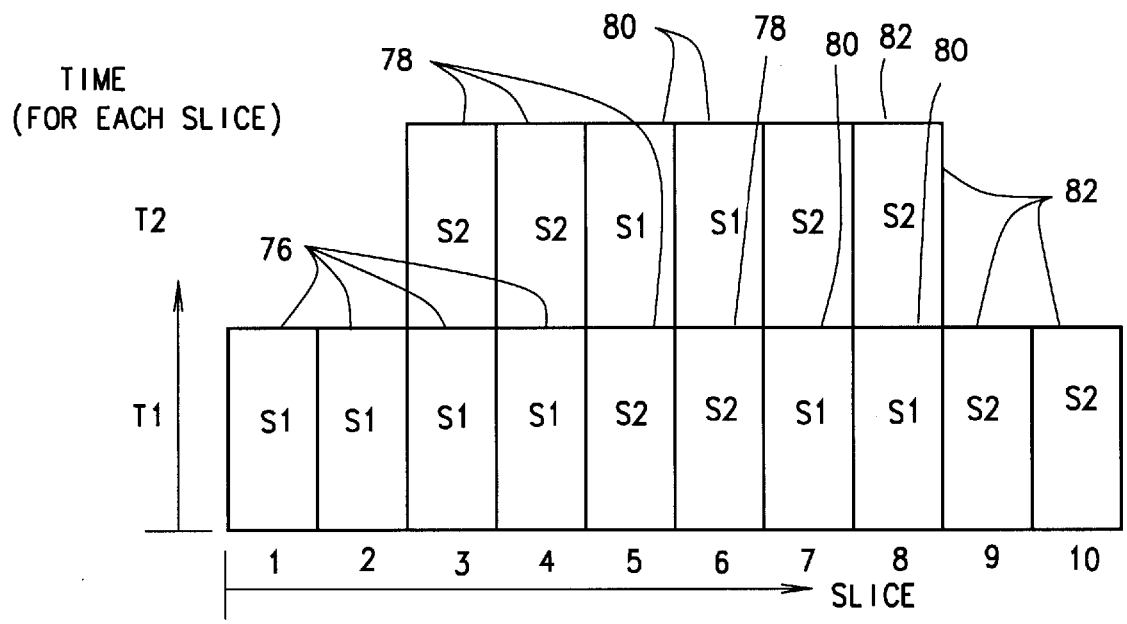
FIG. 7 is a drawing representing view angle sector acquisition in an embodiment in which S=4; I=2; and N=2.

In another embodiment, I is equal to or greater than 1, and less than or equal to S. In this embodiment, N and I must be selected so that $S=N \times I$. In the example illustrated in FIG. 6, S=3, I=1, and N=3. Data for three contiguous slices are obtained each time radiation source 16 is gated on. Thus, the first sectors acquired 68 correspond to view angle sector S1 for slices 1, 2, and 3. Next, additional sectors 70 are acquired after table 46 is stepped I=1 slice, i.e., one slice to the right in FIG. 6. Thus, view angle sector S2 is the next sector of image data to be acquired for slices 2, 3, and 4. For slices 2 and 3, view angle sector S2 is the second sector of image data acquired, as indicated by the notation T2 in FIG. 6. However, sector S2 is the first sector acquired for slice 4, as indicated by the notation T1. During a third sector acquisition 72, table 46 is stepped again and sectors S3 of slices 3, 4, and 5 are acquired. Sector S3 is the third slice acquired for sector 3, as indicated by T3. At this point, slice 3 has a complete set of image data. Sector S3 is the second slice acquired for slice 4, and the first slice acquired for slice 5. In the example of FIG. 6, slices are acquired until acquisition 74, which completes data acquisition for slice 6. As a result of the stepping or indexing of patient's body 22 by motion of table 46 between axial scans, multiple slices of image data are obtained. In the example of FIG. 6, two slices at each end (i.e., slices 1, 2, 7, and 8) are not completed because $I \neq S$. Another example is shown in FIG. 7, where S=4, I=2, and N=2. Image data corresponding to sector S1 are acquired during the first acquisition 76. Subsequent acquisitions 78, 80, and 82 acquire sectors S2, S1, and S2, respectively, with table 46 incremented I=2 slices between acquisitions.

In one embodiment, I<S, and starting angles for all half scans after a first acquisition are constrained by a selection of angle φ for the first acquired sector S1, and successive sector acquisitions after a first acquisition acquire sectors in a rotating order. For example, N=3, and a first acquisition acquires sector S1, a second acquisition acquires sector S2, and a third acquisition acquires sector S3, after which sectors continue to be acquired in an order S1, S2, S3, S1, S2, S3, . . .

Figure 8:
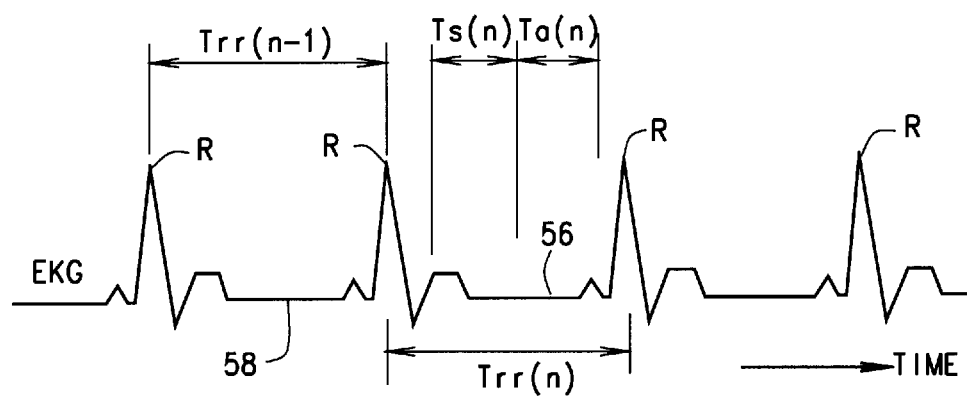
FIG. 8 is a drawing of an EKG signal showing synchronization of image data acquisition with a heart rate of a patient in one embodiment.
Figure 9:
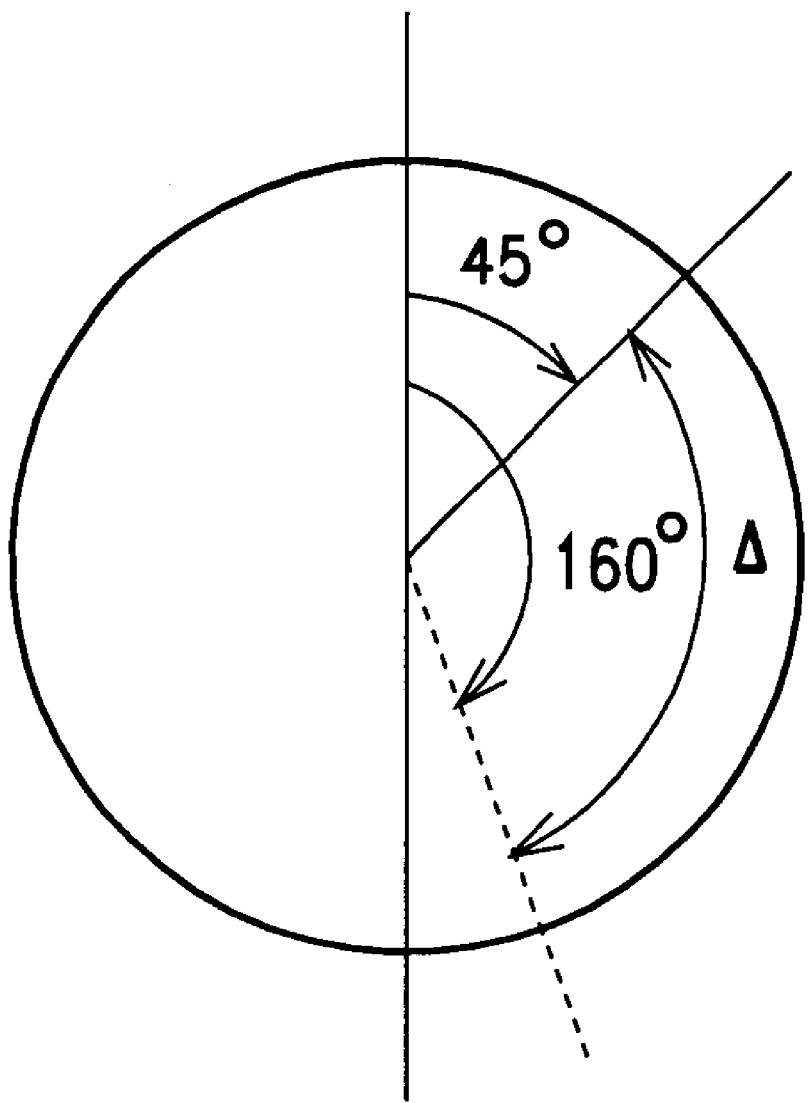
FIG. 9 is a drawing of gantry rotation geometry showing a position of the gantry at a time of an R-peak, and a time at which the gantry is in a position to acquire another sector of data.

FIG. 8 illustrates how data acquisition can be synchronized with the heart rate of patient 22 in one embodiment. As described above, an EKG 58 of patient 22 is taken during acquisition of image data. Because a time when a next R-peak in EKG 58 cannot be known with certainty, computer 36 of CT imaging system 10 estimates a time of each successive R-peak by assuming that a period of a current heart cycle, Trr(n) is equal to a period of the previous heart cycle, Trr(n−1), as measured between R-peaks. (Scanner 10 receives R-peak pulses from EKG 58 and can determine the heart cycle period from these pulses.) During period Trr(n), a time Ts(n) is a time available to start an acquisition at an appropriate view angle for a half-scan sector, Ta(n) is an acquisition time for the half-scan sector, and Ts(n)<Trr(n−1)−Ta(n). A starting view angle for each sector is constrained such that all sectors of a half-scan produce a full half-scan. In one embodiment, image data is acquired over a view angle range slightly larger than the half-scan angle divided by N to provide easier synchronization as well as a view overlap that facilitates blending of sectors for reconstruction. For example, in one embodiment, for a successful scan, a sector scan represented by period Ta(n) is started within interval Ts(n), so that a sector scan completes before the next R peak. Any one of the appropriate start angles are coincident with the interval Ts(n), as a condition giving the start of an acquisition. Given that this condition is satisfied, the sector scan will start when the appropriate coincidence angle is passed by gantry 12. For example, and referring to FIG. 9, if an R-peak arrives at a gantry 12 rotation angle of 45° while gantry 12 is rotating at a 1 second per revolution rate, gantry 12 would be in a position to acquire a next sector Ts=1·(160°−45°)/360°=0.319 seconds later. Ta(n) always occurs after Ts(n).

It will be recognized that a gantry 12 rotation speed must be selected so that the rotation is asynchronous with a heart rate of patient 22.

In one embodiment, false triggering is reduced or eliminated by validating triggers using a defibrillation synchronization line, which is an output of EKG recorder 52. Parametric data is calculated by EKG recorder 52, and R-peaks that are not part of a regular cardiac cycle are rejected, for example, by filtering them from an EKG signal received by computer 36 from EKG recorder 52. For example, R-peaks caused by premature ventricular contraction (PVC) are recognized and rejected because a period between R-peaks is significantly smaller than a heart rate calculated by EKG recorder 52.

From the preceding description of various embodiments of the present invention, it is evident that these embodiments reduce motion artifacts in images produced by cyclical movement of body parts while simultaneously reducing a patient radiation dose required for imaging. Although particular embodiments of the invention have been described and illustrated in detail, it is to be clearly understood that the same is intended by way of illustration and example only and is not to be taken by way of limitation. For example, although cardiac applications are described in detail herein, in other embodiments, other types of physiological gating, for example, respiration or pulse oximetry, are used to reduce motion artifacts. Image data representative of a total view angle greater than a half scan but less than 360° is acquired in other embodiments. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for imaging a portion of a patient's body with a computed tomographic imaging system configured to scan the patient's body at a cyclically varying view angle, the imaging system including a radiation source and detector array providing a fan angle width of image data; said method comprising the steps of:

axially scanning the portion of the patient's body;

gating the radiation source on over less than a 360° view angle cycle of the axial scan;

acquiring image data of the portion of the patient's body during at least a portion of the time the radiation source is gated on; and assembling the acquired image data into an image of the portion of the patient's body.

2. A method in accordance with claim 1 wherein acquiring image data of the patient's body comprises acquiring image data representative of a total view angle of at least a half scan, and assembling the acquired image data comprises assembling image data representative of a total view angle of at least a half scan.

3. A method in accordance with claim 2 wherein acquiring image data of the patient's body comprises acquiring image data representative of a total view angle not less than a half scan but less than 360°, and assembling the acquired image data comprises assembling image data representative of a total view angle of less than 360°.

4. A method in accordance with claim 2 wherein said steps of gating the radiation source on over less than a 360° view angle cycle of the axial scan and acquiring image data of the portion of the patient's body during at least a portion of the time the radiation source is gated on are repeated a plurality of times to collect the image data to be assembled.

5. A method in accordance with claim 4 wherein said repeated steps of acquiring a plurality of sectors of data include steps of acquiring sectors of data representative of different ranges of view angles during different view angle cycles, and assembling the acquired image data into an image of the portion of the patient's body comprises assembling the sectors of data representative of different ranges of view angles.

6. A method in accordance with claim 5 wherein an axial half-scan main view angle is divided into N sectors, where N is a positive integer, each of the N main view angle sectors has a corresponding opposing sector, and said repeated steps of acquiring a plurality of sectors of data comprises acquiring at least one main view angle sector and at least one opposing sector, but only one of each pair of main view angle sector and corresponding opposing sector.

7. A method in accordance with claim 6 wherein said steps of acquiring a plurality of sectors of data comprise operating the imaging system utilizing a fan-para geometry.

8. A method in accordance with claim 7 wherein each acquired opposing sector has a size equal to its corresponding main view angle sector.

9. A method in accordance with claim 6 wherein said steps of acquiring a plurality of sectors of data comprise operating the imaging system utilizing a fan-beam geometry.

10. A method in accordance with claim 9 wherein each acquired opposing sector has a size equal to a size of its corresponding main view angle sector plus an angle in a range from half a fan angle to a full fan angle.

11. A method in accordance with claim 10 wherein each acquired opposing sector has a size equal to a size of its corresponding main view angle sector plus an angle equal to half a fan angle.

12. A method in accordance with claim 5 wherein the radiation source is gated on only during acquisition of a sector of data.

13. A method in accordance with claim 12 wherein the part of the patient body has a cyclical motion, and acquiring sectors of data representative of different ranges of view angles during different view angle cycles comprises the step of acquiring each of the sectors of data representative of different ranges of view angles during substantially the same phase of the cyclical motion of the patient's body part.

14. A method in accordance with claim 13 and wherein said step of acquiring sectors of data representative of different ranges of view angles during different view angle cycles comprises the step of determining, in each view angle cycle, whether to collect a sector, depending upon a range of view angles during which the radiation source is gated on and the cyclical motion of the patient's body part.

15. A method in accordance with claim 5 wherein the computed tomographic imaging system is a single-slice imaging system, and further comprising the step of stepping the patient's body after acquiring, for a first image slice, sectors of data representative of different ranges of view angles during different view angle cycles, to repeat said method to image another slice of the patient's body.

16. A method in accordance with claim 5 wherein the computed tomographic imaging system is a multi-slice imaging system; the step of acquiring image data of the portion of the patient's body during at least a portion of the time the radiation source is gated on comprises obtaining S slices of image data; and acquiring sectors of data representative of different ranges of view angles during different view angle cycles comprises obtaining N different view angles for each of the S slices, one view angle for each of the S slices obtained during each of N repeated steps of gating the radiation source on, and further comprising the step of stepping the patient an increment equal to I times a slice width the slices of image data, where S=N×I.

17. A method in accordance with claim 5 wherein the sectors representative of different ranges of view angles include sectors representative of different, overlapping ranges of view angles.

18. A method in accordance with claim 5 wherein the patient's body part is a heart, said method further comprising the steps of:

monitoring the patient's heart rate while axially scanning the heart; and selecting an axial scan rate asynchronous with the monitored heart rate.

19. A method in accordance with claim 18 wherein monitoring the patient's heart rate comprises the step of determining a period between R-peaks of a cardiac cycle.

20. A method in accordance with claim 19 further comprising the step of validating a trigger with parametric data calculated by a device monitoring the patient's heart rate.

21. A computed tomographic (CT) imaging system configured to scan a patient's body at a cyclically varying view angle, said imaging system including a radiation source and detector array providing a fan angle width of image data; and said imaging system configured to:

axially scan the portion of the patient's body;

gate the radiation source on over less than a 360° view angle cycle of the axial scan;

acquire image data of the portion of the patient's body during at least a portion of the time the radiation source is gated on; and assemble the acquired image data into an image of the portion of the patient's body.

22. An imaging system in accordance with claim 21 wherein said imaging system being configured to acquire image data of the patient's body comprises said imaging system being configured to acquire image data representative of a total view angle of at least a half scan, and said imaging system being configured to assemble the acquired image data comprises said imaging system being configured to assemble image data representative of a total view angle of at least a half scan.

23. An imaging system in accordance with claim 22 wherein said imaging system being configured to acquire image data of the patient's body comprises said imaging system being configured to acquire image data representative of a total view angle not less than a half scan but less than 360°, and said imaging system being configured to assemble the acquired image data comprises said imaging system being configured to assemble image data representative of a total view angle of less than 360°.

24. An imaging system in accordance with claim 22 configured to repeatedly gate the radiation source on over less than a 360° view angle cycle of the axial scan and to acquire image data of the portion of the patient's body during at least a portion of the time the radiation source is gated on to collect image data to be assembled.

25. An imaging system in accordance with claim 24 configured to acquire sectors of data representative of different ranges of view angles during different view angle cycles, and wherein said imaging system being configured to assemble the acquired image data into an image of the portion of the patient's body comprises said imaging system being configured to assemble sectors of data representative of different ranges of view angles.

26. An imaging system in accordance with claim 25 wherein an axial half-scan main view angle is divided into N sectors, where N is a positive integer, each of the N main view angle sectors has a corresponding opposing sector, and said imaging system is configured to acquire a plurality of sectors of data including at least one main view angle sector and at least one opposing sector, but only one of each pair of main view angle sector and corresponding opposing sector.

27. An imaging system in accordance with claim 26 wherein said imaging system is configured to operate utilizing a fan-para geometry.

28. An imaging system in accordance with claim 27 wherein said imaging system is configured to acquire opposing sectors having a size equal to corresponding main view angle sectors.

29. An imaging system in accordance with claim 26 wherein said imaging system is configured to operate utilizing a fan-beam geometry.

30. An imaging system in accordance with claim 29 wherein said imaging system is configured to acquire opposing sectors having a size equal to a size of corresponding main view angle sectors plus an angle in a range from half a fan angle to a full fan angle.

31. An imaging system in accordance with claim 30 wherein said imaging system is configured to acquire opposing sectors having a size equal to a size of corresponding main view angle sectors plus an angle equal to half a fan angle.

32. An imaging system in accordance with claim 25 further configured to gate the radiation source on only during acquisition of a sector of data.

33. An imaging system in accordance with claim 32, wherein the part of the patient body has a cyclical motion, and said imaging system being configured to acquire sectors of data representative of different ranges of view angles during different view angle cycles comprises said imaging system being configured to acquire each of the sectors of data representative of different ranges of view angles during substantially the same phase of the cyclical motion of the patient's body part.

34. An imaging system in accordance with claim 33 wherein said imaging system being configured to acquire sectors of data representative of different ranges of view angles during different view angle cycles comprises said imaging system being configured to determine, in each view angle cycle, whether to collect a sector, depending upon a range of view angles during which the radiation source is gated on and the cyclical motion of the patient's body part.

35. An imaging system in accordance with claim 25 wherein said computed tomographic imaging system is a single-slice imaging system, and further configured to step the patient's body after acquiring, for a first image slice, sectors of data representative of different ranges of view angles during different view angle cycles, and thereafter to image another slice of the patient's body.

36. An imaging system accordance with claim 25 wherein the computed tomographic imaging system is a multi-slice imaging system; and wherein said imaging system being configured to acquire image data of the portion of the patient's body during at least a portion of the time the radiation source is gated on comprises said imaging system being configured to obtain S slices of image data; and said imaging system being configured to acquire sectors of data representative of different ranges of view angles during different view angle cycles comprises said imaging system being configured to obtain N different view angles for each of the S slices, one view angle for each of the S slices obtained during each of N repeated steps of gating the radiation source on, and said imaging system is further configured to step the patient an increment equal to I times a slice width the slices of image data, where S=N×I.

37. An imaging system in accordance with claim 25 wherein the sectors representative of different ranges of view angles include sectors representative of different, overlapping ranges of view angles.

38. An imaging system in accordance with claim 25 wherein the patient's body part is a heart, said imaging system further configured to:
monitor the patient's heart rate while axially scanning the heart; and
select an axial scan rate asynchronous with the monitored heart rate.

39. An imaging system in accordance with claim 38 wherein said imaging system being configured to monitor the patient's heart rate comprises said imaging system being configured to determine a period between R-peaks of a cardiac cycle.

40. An imaging system in accordance with claim 39 further comprising a cardiac monitoring device configured to validate a trigger utilizing parametric data.

* * * * *